United States Patent
Bowers

(10) Patent No.: US 7,700,566 B2
(45) Date of Patent: Apr. 20, 2010

(54) MOSQUITO CONTROL METHOD

(75) Inventor: Doria F. Bowers, Jacksonville, FL (US)

(73) Assignee: University of North Florida, Jacksonville, FL (US)

( * ) Notice: Subject to any disclaimer, the term of this patent is extended or adjusted under 35 U.S.C. 154(b) by 290 days.

(21) Appl. No.: 12/004,287

(22) Filed: Dec. 20, 2007

(65) Prior Publication Data

US 2008/0153777 A1    Jun. 26, 2008

Related U.S. Application Data

(60) Provisional application No. 60/876,818, filed on Dec. 22, 2006.

(51) Int. Cl.
*A61K 31/70* (2006.01)
*A01N 43/04* (2006.01)

(52) U.S. Cl. .......................... 514/25; 514/23

(58) Field of Classification Search ................. None
See application file for complete search history.

(56) References Cited

U.S. PATENT DOCUMENTS

| | | |
|---|---|---|
| 1,738,089 A | 12/1929 | Wallace |
| 2,258,390 A | 10/1941 | Martin |
| 3,244,587 A | 4/1966 | Ayers |
| 3,496,279 A | 2/1970 | Chambers |
| 3,755,597 A | 8/1973 | Abramitis |
| 3,755,598 A | 8/1973 | Howe |
| 3,839,586 A | 10/1974 | Ludvik |
| 3,946,047 A | 3/1976 | Jurd |
| 3,973,040 A | 8/1976 | Jurd |
| 4,525,362 A | 6/1985 | Barer et al. |

*Primary Examiner*—Patrick T Lewis
(74) *Attorney, Agent, or Firm*—Thomas C. Saitta

(57) ABSTRACT

A method of controlling or eradicating mosquito populations in aqueous environments, the method comprising the creation of an aqueous environment having greater than about 2% of sugars such as dextrose, sucrose and fructose in varying ratios. Mosquito larvae fail to develop beyond the second instar stage in solutions of approximately 2% or more, and the time period for the larval stage is prolonged beyond the naturally occurring larval stage time period. Pupation and development into adulthood is reduced in solutions of lesser concentration.

20 Claims, No Drawings

MOSQUITO CONTROL METHOD

This application claims the benefit of the U.S. Provisional Patent Application Ser. No. 60/876,818, filed Dec. 22, 2006.

BACKGROUND OF THE INVENTION

This invention relates generally to the field of mosquito control and eradication, and more particularly relates to methods of mosquito control that prevent metamorphosis of mosquito larvae into pupae and adult mosquitoes.

Mosquitoes at their most benign are annoying and bothersome to humans and animals, the bite of the female mosquito as it seeks blood usually causing an adverse reaction that results in itching, swelling or sores. Of greater concern, mosquitoes at their worst are biological vectors for harmful and deadly pathogens that result in millions of cases of disease and death, such as from malaria, dengue virus and the West Nile Virus. Mosquito-borne viruses, previously more problematic in third world environments, are now by necessity being monitored in the U.S. and other more developed countries.

Mosquitoes inhabit our globe in two distinct environments. The immature stages of the mosquito (larva and pupa) live, feed and metamorphose in aqueous settings until emerging in the winged adult stage, when the mosquito is capable of flight. After hatching from the egg there are four identifiable larval stages, where the mosquito is designated as being a first, second, third and fourth instar larva. The larvae actively feed and shed their exoskeletons with each transition between instars, each instar lasting approximately 1 to 2 days. The larvae then enter the pupae stage, a non-feeding stage where an energetically-demanding metamorphosis into the adult mosquito occurs.

Known methodologies for addressing the mosquito problem include physical abatement, entrapment systems using attractants, mosquitocidal bacteria, larvicides, adulticides, placement of larval predators in water bodies, adhesive traps, citronella candles, mosquito magnets, etc. Many of the methodologies are only successful against small numbers of mosquitoes, while others require the introduction into the general environment of potentially harmful or toxic chemicals, such as for example petroleum based oils or phenols.

It is an object of this invention to provide a method of mosquito control or eradication that is effective during the larval stages prior to emergence of the adult mosquito. It is a further object to provide such a method that does not utilize environmentally harmful chemical agents or the like. It is a further object to provide such a method that does not contaminate the larvae, and further which functions to preclude metamorphosis from the larval stage into the pupal stage, rather than immediately killing the larva, such that they remain an acceptable nutrition source for fish or other animals. It is a further object to provide such a method wherein the larval stage time period is lengthened beyond the norm, such that the larvae remain as a nutritional source for an extended period of time.

SUMMARY OF THE INVENTION

The invention is a method of controlling or eradicating mosquitoes by halting development at the larval stage, i.e., interrupting the insect lifecycle, such that the mosquitoes do not progress from the larval stage into the pupal and adult stages. The method also prolongs the time period during which the larvae remain alive, thereby increasing the amount of time they are available as a food source. The method comprises the step of exposing the immature mosquito larvae to relatively low concentrations of naturally occurring sugars within the mosquito larvae's aqueous environment, as it has been determined that the presence of certain sugars in effective concentrations precludes the transition beyond the larval stage, and in particular precludes transition beyond second instar larvae. The sugars may comprise varying ratios and combinations of fructose, dextrose and sucrose, with effective ratios and combinations mimicking those found in natural nectars such as tangerine, strawberry and white mangrove, for example. Aqueous environments with total sugar concentrations of greater than about 2% have proven to be highly effective. With this methodology, the larvae are not contaminated by harmful or toxic chemicals or pesticides, and are not immediately eradicated so as to remain a food source for fish, the method allowing the larvae to live for up to 14 days without pupating.

DETAILED DESCRIPTION OF THE INVENTION

The method of the invention comprises the introduction of naturally occurring sugars into an aqueous environment containing developing mosquito larvae in an amount effective to prevent pupation. The introduction of effective concentrations of the sugars results in no development of the larvae beyond the larval stage, and usually no development beyond the second instar stage. The introduction of effective concentrations of the sugars also prolongs the larval stage such that the mosquito larvae live up to about 14 days, as opposed to the 4 to 8 day period typical for the larval stage.

The combinations and ratios of sugars experimentally tested to date have been chosen to be generally equivalent to the combinations and ratios of sugars found in natural nectars. For example, a 5% tangerine nectar equivalent solution is created by dissolving approximately 6.2 grams of sucrose, approximately 1.9 grams of dextrose (glucose) and approximately 1.9 grams of fructose in 200 ml of water. This provides a solution that is approximately 3.1% sucrose, approximately 0.95% dextrose and approximately 0.95% fructose. A 5% strawberry nectar equivalent solution is created by dissolving approximately 0.7 grams of sucrose, approximately 5.3 grams of dextrose (glucose) and approximately 4.0 grams of fructose in 200 ml of water. This provides a solution that is approximately 0.35% sucrose, approximately 2.65% dextrose and approximately 2.0% fructose. A 5% white mangrove nectar equivalent solution is created by dissolving approximately 2.2 grams of sucrose, approximately 3.2 grams of dextrose (glucose) and approximately 4.6 grams of fructose in 200 ml of water. This provides a solution that is approximately 1.1% sucrose, approximately 01.6% dextrose and approximately 2.3% fructose. The three sugars sucrose, dextrose and fructose were also tested independently in 5% aqueous solutions. Lower concentrations of 0.5%, 1.0% and above of the nectar equivalent solutions and independent sugars were also prepared and tested.

In tests using *Aedes albopictus* (Asian Tiger Mosquito) or *Aedes aegypti* (Yellow Fever Mosquito) larvae, 5% solutions of each of the tangerine, strawberry and white mangrove nectar equivalent solutions were independently produced using either phosphate buffered saline or pure water in conjunction with the sugars to create the aqueous environments. Larvae were then introduced into the 5% solution aqueous environments in varying numbers. No larvae progressed beyond the second instar of development in the tangerine nectar equivalent solution, the strawberry nectar equivalent solution or the white mangrove nectar equivalent solution. In a further test, liver powder was added to the various solutions above as a nutrient to spur larval development. Again no larvae developed beyond the second instar in any of the environments. In contrast, larvae in a water aqueous environment with no added sugars and in the presence or absence of liver powder food (the control) all developed into adults.

In a test using a 0.5% solution of each of the tangerine, strawberry and white mangrove nectar equivalent solutions as the aqueous environments, pupation and development into adult mosquitoes was reduced to a range of about 53% to 83% for the *Aedes albopictus* larvae, with the tangerine nectar equivalent being the most effective. For the *Aedes aegypti* larvae in a 0.5% solution, pupation and development into adulthood was reduced to a range of about 30% to 80%, with the white mangrove nectar equivalent being the most effective.

At concentrations of approximately 1.0% for each of the tangerine, strawberry and white mangrove nectar equivalent solutions as the aqueous environments, pupation and development into adult mosquitoes was reduced greater than 50%. At concentrations of approximately 3.0% for each of the tangerine, strawberry and white mangrove nectar equivalent solutions as the aqueous environments, pupation and development into adult mosquitoes was totally precluded.

In tests on *Aedes albopictus* larvae, the hardier of the two mosquito types, using each sugar independently as a 5% solution, no larvae developed past the second instar stage for fructose solutions and dextrose solutions, while 13% emerged as adults in the sucrose solution. For 0.5% solutions, 100% of the larvae emerged as adults in the fructose solution, 77% emerged in the sucrose solution, and only 11% developed in the dextrose solution.

Thus, it is evident that creation of an aqueous environment containing greater than about 2.0% of certain natural sugars is effective in significantly reducing or completely preventing pupation and emergence of adult mosquitoes, as development past the second instar: larval stage is precluded or reduced. The methodology does not require the introduction of harmful or toxic chemicals or pesticides into the aqueous environment, and therefore indicates good potential for success in controlling mosquito populations, especially in small volume aqueous environments such as birdbaths, small fish ponds and the like. The larvae are not immediately killed upon introduction of the sugars such that the larvae remain available as a food source for fish, and the normal larval stage is extended up to about two weeks versus the typical 4 to 8 day larval stage.

It is understood that equivalents and substitutions may be obvious to those skilled in the art for certain elements set forth above, and thus the true scope and definition of the invention is to be as set forth in the following claims.

The invention claimed is:

1. A method of prolonging the larval stage of mosquitoes and preventing the transformation of mosquito larvae into pupae comprising the step of creating an aqueous environment for mosquito larvae that comprises at least about 2% of at least one naturally occurring sugar, wherein said mosquito larvae are not immediately killed upon creation of said aqueous environment and whereby said time period of said larval stage is extended beyond the naturally occurring larval stage time period.

2. The method of claim 1, wherein said step of creating an aqueous environment for the mosquito larvae comprises providing at least about 2% of a combination of sucrose, dextrose and fructose.

3. The method of claim 2, wherein said step of creating an aqueous environment for the mosquito larvae comprises providing from about 2% to 5% of a combination of sucrose, dextrose and fructose.

4. The method of claim 2, wherein said step of creating an aqueous environment for the mosquito larvae comprises providing said sucrose, dextrose and fructose in percentages equivalent to the percentages of sucrose, dextrose and fructose occurring naturally in nectars.

5. The method of claim 4, wherein said step of creating an aqueous environment for the mosquito larvae comprises providing said sucrose, dextrose and fructose in percentages equivalent to the percentages of sucrose, dextrose and fructose occurring naturally in the group of nectars consisting of tangerine, strawberry and white mangrove.

6. The method of claim 1, wherein said step of creating an aqueous environment for mosquito larvae prevents the transformation of said larvae from the second instar to the third instar.

7. A method of prolonging the larval stage of mosquitoes and inhibiting the development of mosquito larvae comprising the step of creating an aqueous environment for the mosquito larvae that comprises at least one naturally occurring sugar in an amount effective to prevent transformation of the mosquito larvae into pupae and to extend the larval stage, whereby said mosquito larvae are not immediately killed upon creation of said aqueous environment and whereby said time period of said larval stage is extended beyond the naturally occurring larval stage time period.

8. The method of claim 7, wherein said step of creating an aqueous environment comprises providing at least one of the group of sugars consisting of sucrose, dextrose and fructose, in an amount effective to prevent transformation of the mosquito larvae into pupae.

9. The method of claim 8, wherein said step of creating an aqueous environment for the mosquito larvae comprises providing a combination of sucrose, dextrose and fructose in such amount that said aqueous environment comprises at least about 2% of said combination.

10. The method of claim 9, wherein said step of creating an aqueous environment for the mosquito larvae comprises providing said combination of sucrose, dextrose and fructose in such amount that said aqueous environment comprises from about 2% to 5% of said combination.

11. The method of claim 9, wherein said step of creating an aqueous environment for the mosquito larvae comprises providing said sucrose, dextrose and fructose in percentages equivalent to the percentages of sucrose, dextrose and fructose occurring naturally in nectars.

12. The method of claim 11, wherein said step of creating an aqueous environment for the mosquito larvae comprises providing said sucrose, dextrose and fructose in percentages equivalent to the percentages of sucrose, dextrose and fructose occurring naturally in the group of nectars consisting of tangerine, strawberry and white mangrove.

13. The method of claim 7, wherein said step of creating an aqueous environment for mosquito larvae prevents the transformation of said larvae from the second instar to the third instar.

14. A method of reducing mosquito populations comprising the step of creating an aqueous environment for mosquito larvae that comprises at least one naturally occurring sugar in an amount effective to prevent transformation of the mosquito larvae into pupae and to extend the time period of the larval stage beyond the naturally occurring larval stage time period.

15. The method of claim 14, wherein said step of creating an aqueous environment comprises providing at least one of the group of sugars consisting of sucrose, dextrose and fructose, in an amount effective to prevent transformation of the mosquito larvae into pupae.

16. The method of claim 15, wherein said step of creating an aqueous environment for the mosquito larvae comprises providing a combination of sucrose, dextrose and fructose in such amount that said aqueous environment comprises at least about 2% of said combination.

17. The method of claim 16, wherein said step of creating an aqueous environment for the mosquito larvae comprises providing said combination of sucrose, dextrose and fructose in such amount that said aqueous environment comprises from about 2% to 5% of said combination.

18. The method of claim 16, wherein said step of creating an aqueous environment for the mosquito larvae comprises providing said sucrose, dextrose and fructose in percentages equivalent to the percentages of sucrose, dextrose and fructose occurring naturally in nectars.

19. The method of claim 18, wherein said step of creating an aqueous environment for the mosquito larvae comprises providing said sucrose, dextrose and fructose in percentages equivalent to the percentages of sucrose, dextrose and fructose occurring naturally in the group of nectars consisting of tangerine, strawberry and white mangrove.

20. The method of claim 14, wherein said step of creating an aqueous environment for mosquito larvae prevents the transformation of said larvae from the second instar to the third instar.

* * * * *